United States Patent [19]

Rossomando et al.

[11] Patent Number: 5,158,871
[45] Date of Patent: Oct. 27, 1992

[54] METHOD OF USING MAGNETIC PARTICLES FOR ISOLATING, COLLECTING AND ASSAYING DIAGNOSTIC LIGATES

[75] Inventors: Edward F. Rossomando, West Hartford; Jane Hadjimichael, Simsbury, both of Conn.

[73] Assignee: University of Connecticut, Storrs, Conn.

[21] Appl. No.: 304,341

[22] Filed: Feb. 2, 1989

Related U.S. Application Data

[63] Continuation-in-part of Ser. No. 155,290, Feb. 12, 1988, abandoned.

[51] Int. Cl.⁵ .................. G01N 33/569; G01N 33/553
[52] U.S. Cl. ........................................ 435/7.32; 424/9; 435/971; 436/526; 436/811
[58] Field of Search ............ 424/9; 436/518, 525, 436/526, 828, 548, 501, 503, 506, 536, 538, 540, 543, 547, 125, 177, 811, 824, 825; 435/7, 7.1, 7.2, 7.32, 7.94, 962, 967, 971, 30, 174, 822

[56] References Cited

U.S. PATENT DOCUMENTS

| | | | |
|---|---|---|---|
| 4,279,617 | 7/1981 | Cambiaso et al. | 436/509 |
| 4,452,773 | 6/1984 | Molday | 436/529 |
| 4,486,530 | 12/1984 | David et al. | 436/519 |
| 4,741,999 | 5/1988 | Lenco et al. | 436/519 |

FOREIGN PATENT DOCUMENTS

| | | | |
|---|---|---|---|
| 0030087 | 6/1981 | European Pat. Off. | 436/526 |
| 0194156 | 9/1986 | European Pat. Off. | |
| 55-54157 | 11/1981 | Japan | |
| 2287159 | 12/1987 | Japan | 436/526 |
| 8901161 | 2/1989 | PCT Int'l Appl. | |

OTHER PUBLICATIONS

Vartdal et al., Depletion of T-lymphocytes from Human Bone Marrow Use of Magnetics Monosized Polymer Microspheres, Transplantation (Baltimore) pp. 366-371, 1987 43(3).
Heath, et al., Bacterial Antigens induce Collagnase in Human Gingival Fibroblasts, Infect. Immun. 55(9), 1987, pp. 2148-2154.
Mathur et al., *Fertility and Sterility*, vol. 46, No. 3, pp. 484-488, (1986).
Biological Abstacts vol. 83 (1987), Abstract No. 118315, Ohmori, Y., et al.
Biological Abstracts vol. 84 (1987), Abstract No. 109258, Heath et al.

*Primary Examiner*—Esther L. Kepplinger
*Assistant Examiner*—Susan C. Wolski
*Attorney, Agent, or Firm*—McCormick, Paulding & Huber

[57] ABSTRACT

An in vivo method for preparing, inserting, isolating, collecting and assaying diagnostic ligates present in body fluids. Magnetically responsive particles with attached ligands specific for a particular ligate are introduced into the body fluid. Bonding between the ligand and ligate results in particle/ligand/ligate complexes. The complexes are removed by the application of a magnetic field and the complexes are permitted to cluster. The clusters are then quantitated to determine the concentration of the ligate in the body fluid. Associated materials and devices useful in the practice of this method are also provided.

12 Claims, 3 Drawing Sheets

METHOD OF USING MAGNETIC PARTICLES FOR ISOLATING, COLLECTING AND ASSAYING DIAGNOSTIC LIGATES

CROSS-REFERENCE TO RELATED APPLICATION

This application is a continuation-in-part of U.S. Ser. No. 155,290, filed on Feb. 12, 1988, now abandoned.

BACKGROUND OF THE INVENTION

This invention relates to a method for isolating, extracting and quantitating a specific component present in a fluid. More particularly, the invention provides an in vivo method for isolating and retrieving specific components present in body fluids and indicative of disease states. The present invention further provides a novel assay procedure for quantitating such components. Associated materials and devices useful in the practice of the present invention are also provided.

The body fluids of healthy individuals (both humans and other animals) contain a variety of biochemical components; however, during disease the normal body fluid chemistry may be altered. In some diseases specific components are added to a particular body fluid, while in other disease states specific components normally present in a body fluid are deleted or reduced in concentration. In either case, the concentration of particular body fluid components may be indicative of disease.

A body fluid component indicative of or diagnostic for a disease state may be classified as a ligate. The use of ligates for the diagnosis of disease has been hampered by the lack of a suitable method for accurately determining the concentration of ligates in the body. Such a determination requires isolating and retrieving a ligate from the body fluid of interest. This problem is particularly acute in cases Where the body fluid is located within a body cavity which contains only a small amount of fluid. For example, a diagnostic procedure involving ligates contained in the gingival crevicular fluid involves removing material from a body cavity which contains, at most, one to two microliters of fluid.

Assuming that a ligate can be successfully isolated and removed from the body, precisely determining the concentration of the component has, in many cases, also proven to be particularly difficult. In the past, it has been necessary to employ expensive, cumbersome and time-consuming assay procedures such as radioimmuno-assaying and high performance liquid chromatography.

Accordingly, it is the aim of the present invention to provide a method for successfully isolating and [completely] removing a ligate from a body fluid.

It is a further aim of the invention to provide a simple and inexpensive assaying procedure for determining the concentration of the ligate in the body fluid.

SUMMARY OF THE INVENTION

The present invention meets the above-stated aims by providing an in vivo method for determining the concentration of a ligate in a body fluid. The method comprises the steps of attaching a biological or other molecule (a ligand) specific for the ligate in the body fluid to a magnetically responsive particle. The magnetically responsive particle with the ligand attached is then introduced into the body fluid. The magnetic particle with the attached ligand is permitted to remain in contact With the body fluid for a period of time sufficient for the ligand and ligate to bond and form a magnetic particle/ligand/ligate complex. Once the magnetic particle/ligand/ligate complex is formed, the complexes are retrieved from the body fluid by the application of a magnetic field. After the complexes are collected, they are aggregated to form clusters which are then quantitated to determine the concentration of the ligate in the body fluid.

To further meet the above-stated aims, the present invention contemplates magnetic collecting or harvesting devices designed to be anatomically compatible with each body cavity containing a fluid of interest.

DETAILED DESCRIPTION OF THE INVENTION

Magnetically responsive particles useful in the present invention may be of any type which exhibits a magnetic character and is attracted by a magnetic field. Paramagnetic particles are preferred (i.e., particles which respond to a magnetic field Without resulting permanent magnetism); however, such particles are not required by the method of the present invention. Commercially available particles may be utilized in many applications of the present invention. However, in some instances the particles will have to be specially designed.

Suitable magnetically responsive particles comprise a metal oxide core, usually an iron oxide, surrounded by a sheath of an organic substance to which a suitable ligand may be bound. The composition of the sheath varies depending on what ligand is to be attached and how many attaching sites the sheath provides. The size of the magnetically responsive particles also varies and will depend on the specific application. Two important considerations affecting the choice of particle size are the magnitude of the magnetic field required to retrieve the particles from a specific body cavity in which the fluid of interest is contained and the number of attaching sites the sheath provides. Generally, the magnetically responsive particles will range in size from 1–20 microns.

Magnetic particles, or beads as they are commonly referred to by those skilled in the art, useful in the practice of the present invention include "DYNAL" beads available from Dynal Inc., 45 North Station Plaza, Great Neck, N.Y. "DYNALL" beads are paramagnetic, spherical, polystyrene particles with ferrous oxide centers. They have a uniform diameter of 2.85 or 4.5 microns. The bead's surface functional group, the component on the surface of the bead which couples with the ligand, is an —OH radical and is hydrophyllic. The bead must be "activated" before it can couple with the ligand, and this is accomplished by reacting the hydroxyl group with tosyl chloride.

Other commercially available magnetic particles suitable for practicing the present invention are "SERADYN" beads from Seradyn Inc., P.O. Box 1210, Indianapolis, Ind. and "MAGNISORT" particles from Dupont Co., wilmington, Del. "SERADYN" beads are latex, paramagnetic particles with an iron oxide core. The active surface functional group is —COOH. The beads are 0.7-1.7 microns in size and are non-spherical and non-uniform in shape. The beads require no activation before coupling with the ligand. "MAGNISORT" particles are paramagnetic, chromium dioxide particles coated with silane. The particles have amorphous shapes and are 0.5-5 microns in size. Silane is the functional group, and the particles can be activated by reacting the silane with gluteraldehyde.

The activation time for the commercial particles just noted ranges from several hours to two days. For example, "SERADYN" beads require an overnight activation, while the "DYNAL" beads require two days. However, beads from both Dynal and Dupont can be purchased in activated form.

As noted above, coupled to the sheath surrounding the metal oxide core of the magnetically responsive particle is a ligand capable of binding with a specific ligate present in the body fluid of interest. (Hereinafter the magnetic particle and coupled ligand will be referred to as a MAb particle). The binding interaction may be generally referred to as ligand/ligate binding and includes, for example, but is not limited to, enzyme/substrate, antibody/antigen, receptor/hormone and protein/substrate binding.

The particular ligand to be coupled to the magnetic particle will depend on the specific diagnostic ligate present in the body fluid. That is, only after a ligate has been identified as being diagnostic of a particular disease state can a ligand be developed or selected which will bind with the ligate. For example, two diagnostic ligates associated with periodontal disease and present in the gingival crevicular fluid are interleukin 1 and cachectin. The second of these, cachectin (also known as tumor necrosis factor), was identified through the research of the present inventors as being associated with periodontal disease.

To develop a method for diagnosing a disease, some knowledge of the disease process is required. Periodontal disease, like many bacterially mediated diseases, occurs in a series of steps or stages. One of the first is the activation of macrophages by lipopolysaccharide, a component of the bacterial cell wall. The activated macrophages, in turn, secrete a number of compounds called cytokines which act as signal molecules for fibroblasts, the cells of the connective tissue. In response to this signal, the fibroblasts initiate the production and secretion of collagenase, a particularly destructive enzyme. It is the collagenase which causes the destruction of the tissue seen in periodontal disease.

Cachectin (Cx) is on of the cytokines secreted by the macrophages. The present inventors have studied the effect of this polypetide on dental fibroblasts, and they have established that Cx initiates the production of collagenase. As a precursor to the onset of collagenase secretion, this molecule is an ideal indicator molecule for periodontal disease. Preliminary studies performed with human subjects have shown that those with periodontal disease exhibit detectable levels of Cx while those without any clinical signs of the disease do not. In addition, since Cx levels are expected to increase before the production of collagenase, the ability to detect Cx enables a diagnostician to predict the onset of disease.

Through the us of an ELISA assay the present inventors have established a correlation between periodontal health and the presence of Cx in the gingival crevice. The ELISA procedure used was a modified and improved version of one available in the literature. It was developed using a mouse anti-human Cx monoclonal antibody. A 96 well (Dynatech Immulon I) plate was coated with a 1:1000 dilution of monoclonal antibody (MAb) to cachectin in 0.1 M sodium carbonate/sodium bicarbonate buffer at pH 9.6. The plates were incubated overnight at room temperature (RT), emptied, and carbonate buffer pH 9.6 with 2% fetal calf serum (FCS) was added and incubated at room temperature for four hours or at 4° C. until used. The plates were then washed four times with 0.01 M phosphate buffered saline (PBS) with 0.05% Tween 20 (PBST) with a Biotek automated microplate washer. Cachectin stock solution at a concentration of 0.75 mg/ml was diluted in the PBST to concentration of 1500 picomolar and serial dilutions used in the plates for a standard curve of 1500 picomolar to 2 picomolar. Periopaper (HARCO, Tustin, Calif.) preblocked with 0.1% bovine serum albumin in PBS were used to take gingival samples from patients. The periopapers were laid in the wells with 100 ul PBST-2%FCS and incubated for one hour at 37° C. The periopapers were then removed and the plates washed four times with PBST. Then rabbit anti-cachectin serum diluted 1,100 in PBS-2% FCS was added to each well and incubated one hour at 37° C. followed by washing four times with PBST. A 1:5000 dilution of horseradish peroxidase labeled goat anti-rabbit (Organon Teknika, west Chester, Pa.) in PBST 2% FCS was added to each well, incubated one hour at 37° C., and washed four times with PBST in the washer. Then 150 ul of 2,2'- Azinobis (3-ethylbenzthiazolinesulfonic) (ABTS) at a concentration of 44 mg/ml in water was added to 10 mls of 100 mM citric acid/sodium citrate buffer pH 4.0; 40 ul of 3% hydrogen peroxide was also added to the ATBS-citrate buffer. 100 ul of this solution was then added to each well and color was allowed to develop. The plates were read at 414 nm on a Titertek Multiskan MCC/340, and data analyzed by Skansoft from Linbro on a Basic Time BT/XT. The assay is reproducible and sensitive to 20 pM cachectin or 340 pg/ml and the curve is linear from 1500 pM to 20 pM.

Patients with adult periodontis were selected from outpatients presented for treatment at the University of Connecticut School of Dental Medicine. Individuals were defined as having adult (moderate) periodontitis if they are between the ages of 30 and 60 years and exhibit loss of attachment of at least 4 mm in the presence of 5 mm pocket depth on any surface of at least six permanent teeth. Documentation of periodontal status for the entire periodontia was according to the criteria described by Ranney et al. For inclusion, patients were required to have a negative history for diabetes mellitus, acute necrotizing ulcerative gingivitis and any periodontal therapy within the preceding six months. Clinical signs and/or symptoms of systemic disease or pregnancy also resulted in exclusion. Volunteers from among the student population of the dental school constituted a control population without periodontitis.

Each patient underwent an initial dental evaluation. This examination was performed at the University of Connecticut Clinical Research Center. This evaluation consisted of an intra-and extraoral examination of all teeth caries. In addition, the plaque index (PI) and a gingival index (GI) were determined. Also, measurements of periodontal pockets depth (PD) was determined with a calibrated (to the nearest whole millimeter) periodontal probe. The probe had a diameter of 0.6 mm and a probing "force" of approximately 20 gm was used.

Experimental data was collected and maintained in a computer data base. Each patient file had a patient I.D. number, sampled tooth number, values for Cx in gingival cervicular fluid (GCF, a record of the periodental indices of the sampled teeth (pocket depth, plaque index and gingival index) and notation of current medical status i.e. cancer, etc. All other pertinent details of assay and analysis conditions were also recorded.

Figure 9:
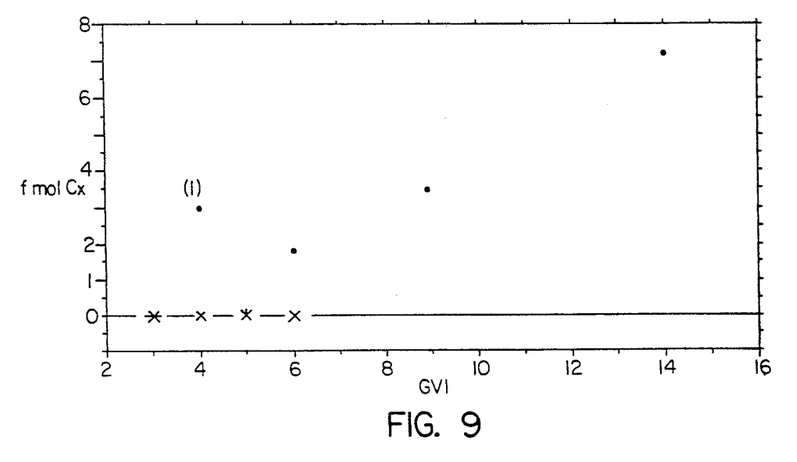
FIG. 9 is a graph representing the correlation between cachectin and periodontal disease.

The correlation between cachectin and periodontal disease is shown in FIG. 9. In this figure the abscissa shows the su GVI) of the gingival index (GI), the plaque index (PI) and the pocket depth (PD) obtained for each site: ($*$) represents 6 samples giving this value, ($*$) represents 5 samples giving this value, (X) represents 4 samples giving this value and (.) represents 1 sample giving this value. The ordinate shows the amount of cachectin from each site. A total of 23 sites were sampled in six patients. These data show an increase in cachectin values when the summation of the indices reaches a value above 5. An unexpectedly high cachectin value was obtained in a relatively health gingiva (see FIG. 9, data point (1)). Since the tooth had a subgingival amalgam filling, the value could be the result of irritation produced by filling.

As noted above, the cytokines, interleukin-1 and cachectin both serve as diagnostic ligates for periodontal disease. Two members of the immunoglobulin G (IgG) class of antibodies, interleukin-1 monoclonal antibody and cachectin monoclonal antibody, respectively provide ligands suitable for binding these ligates.

The attachment between the ligand and the magnetic particle must be sufficiently strong to retain the ligand on the particle while both are introduced into the body fluid and during the binding interaction between the ligand and ligate. Furthermore, the attachment between the particle and the ligand must be sufficiently strong to permit the particle/ligand/ligate complex to be removed from the body as a unit. The nature of the attachment will depend primarily on the chemical structure of the ligand. For example, the monoclonal antibodies noted above may be covalently coupled directly to the magnetic particle in a substitution reaction. Alternatively, a linking medium, such as a protein A linker, may be used to couple the IgG to the magnetic bead.

The time required for the coupling reaction, i.e., the attachment of the ligand to the activated magnetic particle, varies from several hours to several days. The type of active surface functional group presented by the particle affects the coupling reaction. For example, IgG is more easily coupled to carboxyl groups than to hydroxyl groups. Coupling efficiency assays, using $^{125}I$ labeled IgG, showed that for the various magnetic particles noted above, DYNAL beads bound 26.7% of the available IgG, SERADYN beads bound 50.7% and MAGNISORT particles bound 67% of the available IgG. It should be noted that the assay results were due, at least in part, to differences in the total surface area of each of the bead preparations.

After the coupling reaction is complete, the magnetically responsive particles with their attached ligand are introduced into the body fluid containing the diagnostic ligate. In the case of periodontal disease, where either cachectin or interleukin-1 is the diagnostic ligate, a slurry of the MAb particles is prepared and introduced into the sulcus with a microdispenser.

After the magnetic particles with their attached ligand have been introduced into the body fluid and the binding reaction between the ligand and the diagnostic ligate is complete, the magnetic particle/ligand/ligate complexes must be removed from the body. This is accomplished by means of a magnetic gathering or harvesting device which will attract and retain the complexes by applying a localized magnetic field. The magnetic harvesting device must be anatomically compatible with the body cavity containing the body fluid into which the magnetic particles have been introduced. In addition, the harvesting device must be capable of applying a magnetic field which corresponds to the size of the magnetic particle being utilized. Thus, each application of the present invention may require its own magnetic harvesting device. However, in general these devices are hand held and comprise an electromagnet and a tip suitable for insertion into the body cavity.

Figure 1:
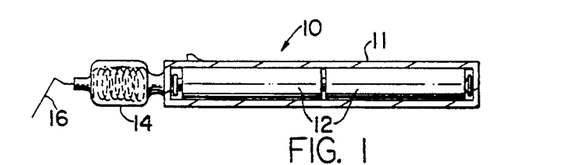
FIG. 1 illustrates a magnetic harvesting device for retrieving magnetic particle/ligand/ligate complexes from the gingival crevice.

FIG. 1 illustrates an electromagnetic harvester 10 designed for removing magnetic particle/ligand/ligate complexes from the gingival crevice. The harvester comprises a handle 11 which houses a power supply consisting of two 1.25 volt batteries 12,12. The harvester further comprises an electromagnetic coil 14 having 350 turns of 24 gauge copper wire, and a tip 16. The tip illustrated in FIG. 1 is shaped like a standard periodontal probe; however, several other tip designs, such as a shovel-shaped tip, are also effective.

Standardized tests show that the magnetic harvester produces a magnetic field capable of moving a 0.63 g weight 6.7 cm. A magnetic field one third this strength is about 25% efficient at removing magnetic beads from a test solution. A field eight times the strength of that produced by the harvester is 100% efficient at removing the beads from the same solution. Those skilled in the art will readily appreciate that the harvester's field strength may easily be adjusted to account for variables such as the type of magnetic particles utilized and the particular body cavity from which the complexes must be removed.

Figure 2:
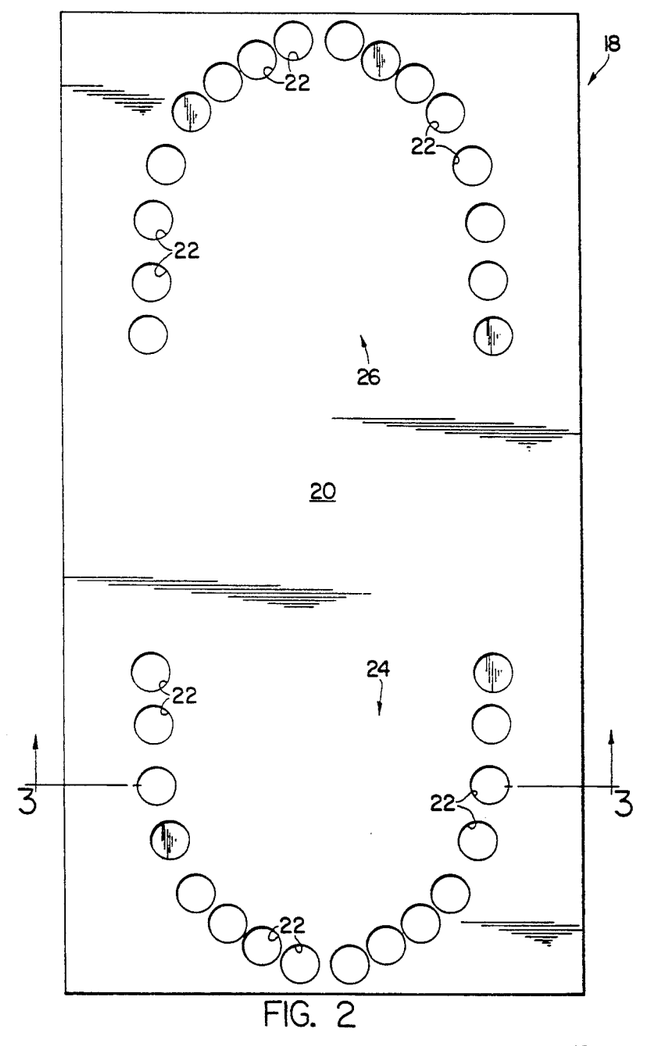
FIG. 2 illustrates a tray for collecting the complexes.
Figure 3:
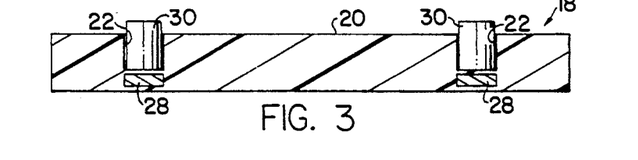
FIG. 3 is a sectional view taken along line 3—3 of the tray shown in FIG. 2.

For the diagnosis of periodontal disease, the present inventors found it necessary to design and fabricate a special tray for collecting the magnetic particle/ligand-/ligate complexes from the harvester's tip. FIG. 2 illustrates the collection tray 18 which comprises a generally rectangular sheet 20 composed of a plastic material such as lucite. A plurality a wells 22,22 are formed in the sheet 20. There is a well representing each tooth, and the wells are arranged in two arches 24 and 26, arch 24 corresponds to the lower set of teeth and arch 26 corresponds to the upper set of teeth. As illustrated in FIG. 3, a permanent magnet 28 is place in the bottom of each well to facilitate collection of the complexes.

Each well contains a removable plastic cup 30 to which 2.5 ml of buffer, such as 0.05 M Tris HCL, pH 7, has been added. The tip of the harvester with the attached complexes is introduced into the buffer; the complexes are removed from the tip with a nylon bristle brush rotating at slow speed and suspended in the buffer. A standard dental engine (slow speed hand piece) may be used to rotate the brush; however, care must be taken to avoid excessive vortex formation, foaming and splashing.

Once the magnetic particle/ligand/ligate complexes have been removed from the body, the concentration of the ligate in the body fluid is quantitated. The present invention utilizes a simple and direct assay procedure which relies on the aggregation of the complexes into clusters at least large enough to be visible under a low power microscopic field. As stated above, the particle/ligand/ligate complexes extracted from the body fluid are suspended in the buffer. To this suspension is added a second suspension of aggregating particles.

The aggregating particles are prepared by coupling a magnetically responsive particle with a ligand specific for the diagnostic ligate but different from the ligand used for in vivo bonding. (Hereinafter the magnetic particle and the ligand employed for the aggregating particle will be referred to as a PAb particle). For example, as noted previously, where cachectin is the ligate of interest, monoclonal antibody is used as the ligand for in vivo bonding, and polyclonal antibody is used to form the aggregating particle. Since ligates normally include at least two sites at which a ligand may be bound, the ligand of the aggregating particle will attach to the ligate at one or more unoccupied ligand binding sites. Thus, a magnetic particle/ligand/ligate—aggregating particle cluster is formed.

Figure 4:
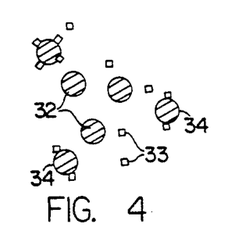
FIG. 4 is a schematic representation of magnetic particle/ligand/ligate complexes.

FIG. 4 illustrates diagrammatically the magnetic particle/ligand/ligate complexes. As stated previously, the complexes comprise a ligand coupled to a magnetic particle and a ligate bound to the ligand. In FIG. 4, the magnetic particles and coupled ligand are designated by numerals 32,32, the unbound ligate as 33,33 and the entire complex is designated by numerals 34,34.

Figure 5:
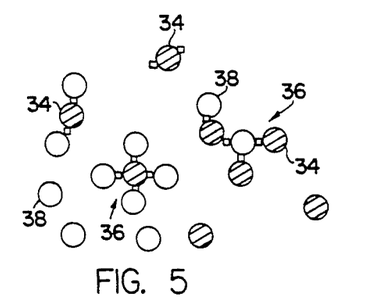
FIG. 5 is a schematic representation of magnetic particle/ligand/ligate—aggregating particle clusters.

FIG. 5 illustrates diagrammatically the magnetic particle/ligand/ligate-aggregating particle clusters. The clusters 36 comprise at least one complex 34 and at least one aggregating particle 38. As shown in FIG. 5, the clusters may exhibit a linear, rosette or branched pattern.

The overall quality of the cluster assay is affected by a number of factors. One such factor is non-specific cluster formation. Functional groups on the magnetic particles which are not blocked by IgG may couple with body fluid components that do not bind with the diagnostic ligate at all or do so non-specifically. When this occurs, clusters may form which do not include the diagnostic ligate, thus obscuring the results of the assay.

It has been found that non-reactive proteins added to the suspension suppress non-specific clustering. The most preferred such protein is bovine serum albumin (BSA). Alternatively, surfactants, such as Tween 20 or Trtion X may be added to the suspension. However, in general it has been found that surfactants are less effective at reducing non-specific clustering than are non-reactive proteins. Finally, the ionic strength and chemical content of the buffer were varied in an attempt to reduce non-specific clustering. NaCL, KCL, Tris HCL and monobasic/dibasic potassium phosphate all proved effective. However, a 0.5 M Tris HCL solution at pH7.0 with 0.1% BSA is the most preferred combination for suppressing non-specific cluster formation.

Attempts were made at using different magnetic particles for the monoclonal and polyclonal antibody attachments in the same assay. It was found, however, that even with the use of the suppression techniques described above, different beads with different surface functional groups formed clusters based on functional surface group interactions rather than antibody/ligate interactions. The results indicate that different magnetic particles can not be used together in the same assay.

The size and shape of the magnetic particles also affects the quality of the cluster assay. For example, the 0.7-1.7 micron size and non-spherical shape of SERA-DYN beads make the individual beads difficult to visualize at a magnification of 30×. Furthermore, random aggregation occurred in blank samples which made quantitation of the clusters difficult. The MAGNISORT" particles are 0.5 to 5 microns in diameter. The 0.5 micron beads cannot be seen at 30×magnification, and the amorphous shape of the particles is not conducive to clustering.

It was finally determined that DYNAL beads are the most preferred particles for the assay; the 2.85 micron size and spherical shape of the DYNAL beads proved to be very effective at promoting cluster formation. For example, when diluted into a 0.05 M Tris-HCL buffer at neutral pH, the beads form rosettes with 22.5 fmol cachectin and a 20:1 ratio of FAb to MAb beads.

As noted above, the clusters formed should be large enough to be visible under a low power microscopic field. Clusters of this size permit direct counting of the clusters, or, the microscopic image of the clusters may be recorded on a suitable storage medium for subsequent counting by computer. Alternatively, the clusters may be counted by devices of the type used to count cells, which may be adjusted for particles of varying sizes.

Where microscopic observation is employed, clustering is defined as the appearance of groups of four or more beads when using a non-computer assisted counting procedure. A net micrometer disk in the ocular of the microscope defines the area to count.

Figure 6:
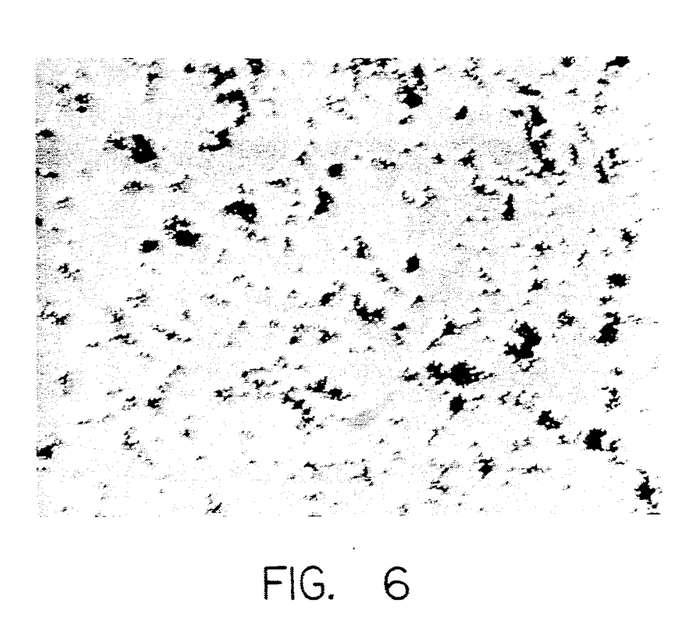
FIG. 6 is a photograph of magnetic particle/ligand-/ligate—aggregating particle clusters.
Figure 7:
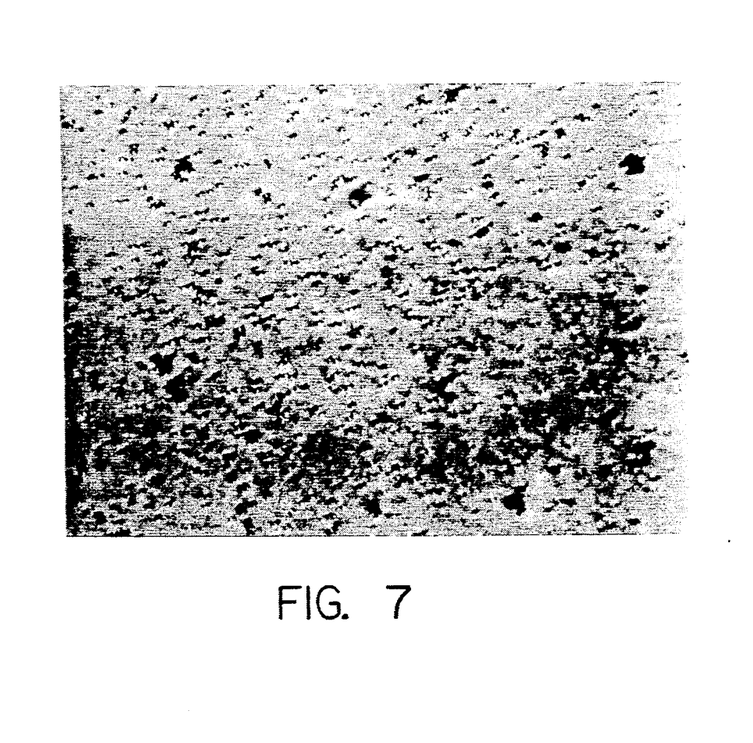
FIG. 7 is a photograph of non-specific clustering in a control sample.

FIG. 6 is a photograph of the clustering of the MAb beads and PAb beads in the presence of 22.5 fmol cachectin. FIG. 7 is a photograph of the low level of non-specific clustering in a control sample. The photographs were taken with Hoffman phase contrast optics at 300×magnification.

Figure 8:
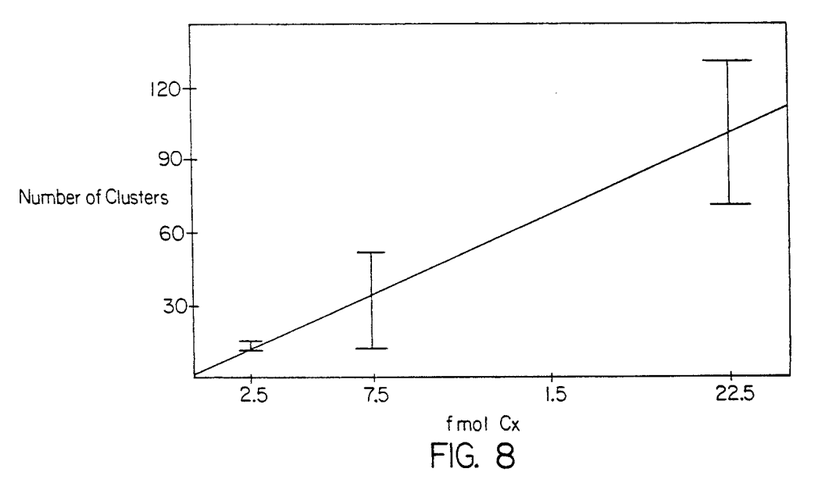
FIG. 8 is a calibration curve wherein the number of clusters is plotted as a function of cachectin concentration.

The number of clusters was found to increase with the concentration of cachectin. The detection limit was determined to be 2.5 fmol. However, it is expected that 10 to 100 fold lower amounts will be detectable with further optimization of the assay. The calibration curve of the number of bead clusters as a function of femptomoles of cachectin is shown in FIG. 8. In FIG. 8, the number of clusters of 4 or more beads in 10 calibrated microscopic fields was plotted against the known amount of cachectin in the samples.

The method of the present invention is illustrated by the following examples.

EXAMPLE 1

Example I illustrates a procedure for the attachment of cachectin/TNF Cx) monoclonal antibodies to magnetic particles containing Protein A linker.
1. Pipet 1 ml Protein A coated magnetically responsive particles
   (approx. 5 mg/ml) into a vial.
2. Collect particles on bottom of vial with magnet and remove liquid.
3. Add 1 ml 0.1 M Na2HP04 pH 8.0.

4. Add 140 ul Cx monoclonal antibody at 0.5 mg/ml to vial.
5. Incubate at room temperature for 2 hrs with shaking.
6. wash three times in 0.1 M Na2HP04 pH 8.0 as in step 2.
7. After decanting the third wash resuspended in 4 ml Tris Buffered Saline (TBS), pH 7.5.

Particles with attached ligand are now ready for binding of cachectin in fluid.

EXAMPLE II

Example II illustrates the preparation of aggregating particles by the attachment of polyclonal antibodies to magnetic particles for use in the cluster assay.

1. Pipet 1 ml Protein A coated particles (approx. 5 mg/ml) into a vial.
2. Collect particles on bottom of vial with magnet and remove liquid.
3. Add 1 ml 0.1 M Na2HP04 pH 8.0.
4. Add 140 ul Cx polyclonal antibody (rabbit anti Cx) at 0.5 mg/ml to vial.
5. Incubate at room temperature for 2 hrs with shaking.
6. wash three times in 0.1 M Na2HP04 pH 8.0 as in step 2.
7. After decanting the third wash resuspend in 4 ml Tris. Buffered Saline (TBS , pH 7.5.

Aggregating particles are now ready for use in the cluster assay.

EXAMPLE III

Example III illustrates how the cachectin (Cx) bound to the MAb particles can be identified by clustering of the particle.

1. Prepare Cx solution of 5 ug/ml TBS.
2. Pipet 10 ul Cx MAh particles into wells.
3. Dilute from 0 to 10 ul of Cx solution (0 to 50 ng Cx) into wells.
4. Adjust wells to 50 ul with TBS.
5. Incubate at room temperature with gentle rocking for 2 hours.
6. Add 10 ul aggregating particles to each well.
7. Pipet 90 ul TBS to wells corresponding to the primary wells.
8. Pipet 10 ul from each primary well to a corresponding secondary well (a 1:10 dilution).
9. Incubate at room temperature with gentle rocking for 2 hrs.
10. Observe wells under low power by bright field microscopy.
11. Score wells for aggregation.

EXAMPLE IV

Example IV illustrates that the magnetically responsive particles can be placed in the gingival crevice of a monkey and retrieved with an electromagnet.

1. Fill a 1 ml syringe with 1 ml of a slurry of particles.
2. Using an anesthetized monkey, isolate a maxillary quadrant with cotton rolls.
3. Place flexible narrow bore tubing on tip of syringe and place tubing at mouth of gingival crevice and below edge of gum tissue.
4. Dispense solution from syringe into crevice.
5. Pass hand-held electromagnet (able to generate 3750 Gauss) having an attached sterile tip with tip length of 8 mm and a round 4 mm diameter end over gingival crevice. Tip of magnet should be in contact with tissue. Particles will be observed to collect on the tip of the magnet.
6. Number of particles collected can be determined by counting them directly under a microscope using a "Bright-Line" calibrated counting chamber.

EXAMPLE V

Example V illustrates manual counting of clusters. Clusters are visualized using an Olympus inverted microscope with Hoffman phase contrast capabilities and an attached Polaroid camera. Eppendorf 1.5 ml polypropylene tubes are used as incubation vessels. Final solutions are transferred to glass slides with cover slips or 96 well Linbro plates are used as reaction vessels. MAb beads are diluted to a concentration on the order of $1\times10^5$ beads /ml for use and reacted with cachectin solution of 1500 pM, 500 pM and 167 pM. These mixtures are allowed to incubate for 3 min. at room temperature, then reacted for 10 min. following the addition of polyclonal beads at 20 times the MAb bead concentration. Linbro 96 well plates were found to be best suited for the assay due to the least distortion of the flat well bottom when compared with other manufacturers. Plastic plates were found best suited for use because of cachectin's affinity for glass. Photographs in FIG. 6 shows clusters obtained with this procedure.

EXAMPLE VI

Example XI illustrates a procedure for the attachment of cachectin/TNF (Cx) monoclonal antibodies to magnetic particles.

1. Pipet 200 ul of preactivated magnetically responsive particles (approx. 30 ug/ml) into a vial.
2. Collect particles on bottom of vial with magnet and remove liquid. Resuspend beads in 1 ml of water.
3. wash 1×with water, vortex and repeat step 2.
4. Prepare monoclonal antibody (MAb) solution by dissolving antibody in 0.2 M borate buffer, pH 9.5 at final concentration of 150 ug/ml.
5. Add 1 ml of MAb solution to 1 ml of bead solution (from step 2).
6. Incubate at room temperature for 24 hrs with slow end-overend rotation.
7. Collect beads with magnet and discard supernatant solution.
8. wash with 1 ml 0.1 M phosphate buffered saline (pH 7.4) for 10 min.
9. wash with 1 ml 1 M ethanolamine.HCl (pH 9.5) containing 0.1% Tween 20 for 2 hrs.
10. wash with 1 ml 0.05 M Tris in 0.1 M NaCl, 0.1% boving serum albumin BSA), 0.01% merthiolate, 0.1% Tween 20 pH 7.5 for about 12 hrs.
11. wash with 1 ml buffer as described in step 11, without Tween 20, for 2 hrs.
12. Collect particles, discard supernatant solution and resuspend in 200 ul of buffer containing 0.05 M Tris in 0.1 M NaCl with 0.1% BSA and 0.01% merthiolate. The particles are stable for at least 6 mo. When stored at 4° C.

EXAMPLE VII

Example VII illustrates the preparation of aggregating particles by the attachment of polyclonal antibodies (PAb) to magnetic particles for use in the cluster assay.

1-3. As in example VI.

4. As above except use PAb.

5-12. As in example VI.

EXAMPLE VIII

Example VIII illustrates how the Cx bound to the MAb particles can be identified by clustering of the particles.
1. Prepare Cx stock solution to contain 3000 nM of Cx in a buffer containing 0.05 M Tris-HCl (pH 7.5) with 0.01% BSA.
2. Use MAb particles prepared in example 6. Collect beads from storage solution with magnet. Remove storage buffer. Resuspend beads in Tris-HCl buffer (pH 7.5). Dilute this suspension 1:25 in Tris buffer and again 1:10 in the same buffer. Pipet 5 ul of this MAb particle suspension into wells.
3. Make serial dilutions of stock Cx solution (prepared in step 1) such that two new solutions are prepared, one containing 1000 nM and another 333 nM Cx. Prepare an additional solution, the blank to contain the buffer only.
4. Add 10 ul from each of the three solutions containing Cx and 10 ul of the dilution buffer from step 1 into wells containing MAb prepared in step 2.
5. Incubate at room temperature for 5 min.
6. Use PAb particles prepared in example 7. Collect beads from storage solution, remove storage buffer and resuspend beads in Tris-HCl (pH 7.5). Dilute 60 ul of this solution into 500 ul of Tris buffer then 30 ul of this solution into 300 ul of buffer. Add 30 ul aggregating particles (PAb) to each well.
7. Incubate at room temperature for 5 min.
8. Observe well under low power by Hoffman phase microscopy.
9. Count clusters composed of 4 or more beads in field defined by "net" micrometer. Repeat counts 10 times and average. See FIG. 6 for photograph of microscopic field showing clusters. See FIG. 7 for photograph of microscopic field showing the absence of clusters.
10. Generate graphical representation of data obtained from step 9 by plotting number of clusters observed at each of the three concentrations used in step 4 (ordinate) as a function of the three concentrations (abscessa). The number of clusters observed in the blank solution has been subtracted from each of the experimental determinations. A representative graph is shown in FIG. 8.

EXAMPLE IX

Example IX illustrates that magnetically responsive particles can be placed in the gingival crevice of a human and retrieved with an electromagnet.

1. Fill a 25 ul syringe (Drummond "sequencing" pipet) with approx 15 ul of a slurry of MAb particles prepared in example 6.
2. Using a human subject, isolate a quadrant with cotton rolls.
3. Place the flexible plastic tip of the syringe at mouth of gingival crevice and below edge of gum tissue.
4. Dispense solution from syringe into crevice.
5. Place tip of electromagnetic harvester (illustrated in FIG. 1) in gingival crevice. Activate magnet and particles will be observed to collect on the tip of the magnet.
6. Remove harvester from subjects mouth and bring to tray show in FIG. 2. Insert tip into well shown in FIG. 3 and after shutting off magnetic field, remove particles from tip with slowly rotating bristle brush.
7. Remove excess beffer.
8. Add PAb particles prepared in example VII. Clusters will form as described in example 8.
9. Amount of Cx recovered from gingival sulcus can be determined by counting clusters directly under a microscope using low power Hoffman phase microscopy as described in example VIII.

The present invention has been disclosed by way of example and not by way of limitation. Many modifications and variations of the invention may be made without departing from the scope of the appended claims. For example, while the invention as set forth above is directed to an in vivo method for diagnosing disease states, it is also well suited for isolating and retrieving specific compounds present in industrial processes and the environment. The invention can be applied to veterinary medicine and is useful for the delivery of medications. Such applications are particularly important where industrial waste fluids contain toxic or other environmentally harmful compounds.

We claim:

1. A method of determining the amount of a ligate in a fluid which comprises:

attaching a first ligand comprising a monoclonal antibody specific for the ligate to magnetically responsive particles;

introducing the magnetically responsive particles with attached first ligand into the fluid;

allowing the magnetically responsive particles with attached first ligand to bind to the ligate so that magnetic particle/ligand/ligate complexes are formed;

retrieving the complexes from the fluid by means of a magnetic field;

resuspending the retrieved complexes;

aggregating the resuspended complexes to form suspended clusters by adding aggregating particles to said complexes, said aggregating particles comprising a magnetically responsive particle with an attached second ligand which specifically binds to said ligate, wherein said second ligand is different from said first ligand and wherein said clusters comprise at least one of said complexes and at least one of said aggregating particles;

allowing the suspended clusters to settle onto a support surface, and determining the amount of oligate retrieved from the fluid by visually detecting said clusters with the aid of a microscope.

2. The method of claim 1 wherein the step of attaching the ligand is further characterized in that the ligand is attached to the magnetically responsive particle through a protein A linker.

3. The method of claim 1 wherein the step of determining the amount of ligate retrieved from the fluid is further characterized in that the clusters visible under the microscope form an image which is recorded on a suitable storage medium and the number of clusters present in the image is determined by computerized counting.

4. A method of screening for periodontal disease which comprises:

attaching a first ligand comprising a monoclonal antibody specific for a ligate present in the gingival crevicular fluid and indicative of periodontal disease, which is selected from the group consisting of cachectin and interleukin 1, to a magnetically responsive particle;

introducing the magnetically responsive particle with attached first ligand into the gingival crevicular sulcus;

allowing the magnetically responsive particles with attached first ligand to bind to the ligate so that magnetic particle/ligand/ligate complexes are formed;

retrieving the complexes from the gingival crevicular sulcus by means of a magnetic field;

resuspending the retrieved complexes;

aggregating the resuspended complexes to form suspended clusters by adding aggregating particles to said complexes, said aggregating particles comprising a magnetically responsive particle with attached second ligand which specifically binds to said ligate, wherein said second ligand is different from said first ligand, and wherein said clusters comprise at least one of said complexes and at least one of said aggregating particles;

allowing the suspended clusters to settle onto a support surface, and determining the amount of the ligate indicative of periodontal disease retrieved from the gingival crevicular fluid by visually detecting said clusters with the aid of a microscope.

5. The method of claim 4 wherein the step of retrieving the particle/ligand/ligate complexes is further characterized in that the complexes are retrieved by means of a magnetic harvester comprising a hand-held electromagnet having an attached tip anatomically compatible with the oral cavity.

6. The method of claim 4 wherein the step of attaching the first ligand to the magnetically responsive particle is further characterized in that the first ligand is an immunoglobulin G monoclonal antibody.

7. The method of claim 4 wherein the step of aggregating the complexes to form clusters is further characterized in that the second ligand comprises polyclonal antibodies which specifically bind to the ligate indicative of periodontal disease.

8. The method of claim 4 wherein the step of aggregating the complexes to form clusters is further characterized in that the complexes are resuspended in a buffer.

9. The method of claim 8 further characterized in that said buffer is 0.5 m Tris HCL.

10. The method of claim 8 further characterized in that the buffer includes a nonimmunologically-reactive protein.

11. The method of claim 10 further characterized in that said nonimmunologically-reactive protein is bovine serum albumin.

12. The method of claim 8 further characterized in that the buffer includes a surfactant.

* * * * *